(12) United States Patent
Logue et al.

(10) Patent No.: US 6,580,267 B2
(45) Date of Patent: Jun. 17, 2003

(54) METHOD OF EXTENDING THE UTILITY OF AN INTEGRAL DRIVING-SENSING POT-CORE HALF EDDY CURRENT PROBE

(75) Inventors: Delmar Leon Logue, Herrick, IL (US); Stephen John Logue, Taylorville, IL (US)

(73) Assignee: Logue Sensor Co., Herrick, IL (US)

( * ) Notice: Subject to any disclaimer, the term of this patent is extended or adjusted under 35 U.S.C. 154(b) by 0 days.

(21) Appl. No.: 09/873,838

(22) Filed: Jun. 4, 2001

(65) Prior Publication Data

US 2002/0008512 A1 Jan. 24, 2002

Related U.S. Application Data

(63) Continuation-in-part of application No. 09/419,140, filed on Oct. 15, 1999, now Pat. No. 6,271,664, and a continuation-in-part of application No. 09/467,599, filed on Dec. 20, 1999, now Pat. No. 6,265,871.

(51) Int. Cl.[7] .................. G01N 27/72; G01R 33/12
(52) U.S. Cl. ............................... 324/240; 324/225
(58) Field of Search ........................ 324/240, 225, 324/232, 241, 243, 238, 239

(56) References Cited

U.S. PATENT DOCUMENTS 6,271,664 B1 * 8/2001 Logue .................... 324/240

* cited by examiner

Primary Examiner—Walter E. Snow

(57) ABSTRACT

An axial direction groove is formed in a high permeability toroidal core taking the form of a pot core half with a mounting hole, a high cross-section ratio copper casing being tightly fit around core circumference, having poly-phase excitation windings shuttled through the mounting hole to encompass both the copper casing and the pot-core, forming an integral driving-sensing eddy current probe. A naked pot-core is wound as an integral driving-sensing probe. Poly-phase excitation of the probe is mesh-connected as a gramme-ring.

4 Claims, 3 Drawing Sheets

METHOD OF EXTENDING THE UTILITY OF AN INTEGRAL DRIVING-SENSING POT-CORE HALF EDDY CURRENT PROBE

CROSS-REFERENCE TO RELATED APPLICATIONS

This Patent Application is a continuation-in-part of patent application Ser. Nos.: Ser. No. 09/419,140 filed Oct. 15, 1999 now U.S. Pat. No. 6,271,664B1 and Ser. No. 09/467,599 filed Dec. 20, 1999 now U.S. Pat. No. 6,265,871B1.

BACKGROUND OF THE INVENTION

1. Field of the Invention

Earlier Logue patents refer to the related devices as "polar coordinates sensor" i.e. a hemispherical rotating field generator.

This invention employs a toroidal wound pot-core half generating a rotating magnetic field fringing through the excitation turns.

2. Related Art

Tesla U.S. Pat. No. 382,280 disclosed a ring built up of insulated annular iron plates and wound with poly-phase distributions forming an early rotating field stator for generator/motor use. Field utility was limited to the winding window of the toroidal stator. In the cited Logue patent applications the rotating hemispherical flux fringing from the plane of this toroidal stator (pot-core half) was utilized for inducing eddy currents in conducting workpieces e.g. aircraft splice joints. The driving flux is directly coupled from the toroidal plane to the workpiece through the poly-phase excitation turns.

Oscillatory Signal Build-up

The polar coordinates signal disclosed in the ascending Logue patents is actually formed by successive revolutions of the hemispherical driving field acceleration; the axis of which is displaced by an asymmetry (flaw) in the eddy current reflection. This is a rotary type of parametric pumping. Acceleration of the driving field revolutions is explained and illustrated in Logue U.S. Pat. No. 5,909,118 (obviously frequency modulation).

SUMMARY OF THE INVENTION

A primary object of the invention is a tighter focusing of the probe pattern fringing from the toroidal driving plane. Tightly fitting a copper toroid concentrically around a pot-core half eliminates the flux spilling gap resulting from a previous method of winding the excitation distributions around the pot-core first (Logue U.S. Pat. No. 6,265,871). An all encompassing toroidal excitation winding method is show in FIG. 1, in which the poly-phase distributions thread through the toroidal window, encircling the pick-up coil, driving toroid and the mentioned thick copper toroid (a Lenz lens). A second object of the invention is an arrangement of concentric pot-core halves on increasing radii for generating at least two radii of concentric eddy current hemispheres in a conducting workpiece, the pick-up coil of each pot-core generating a flaw signal in response to a flux asymmetry. This increasing driving\sensing radii equals differing depths of eddy current excitation\reflection. As taught in Logue U.S. Pat. No. 6,265,871 individuality of predetermined angular velocities is provided between concentric toroidal cores (radii isolation of excitation current phase/amplitude is obviously possible). A further object of the disclosure is an excitation method similar to well known television picture tube electron beam/s deflection by a predetermined current modulation of the toroidal yoke windings (toroidal probe) i.e the x-y excitation axes of a resultant vectorial fringing magnetic field. In the light of television, radar and Logue U.S. Pat. Nos. 6,265,871 6,229,305 6,271,664 6,271,664 the underling principles of this method are understood.

The preferred pick-up assembly to date is a pot-core half with a pick-up coil having many turns of small guage magnet wire e.g. 42 ga., wound around the central pole (184, FIG. 1) filling the annular coil space 179. For more complete annular space filling of the pick-up core, flat small guage magnet wire may be spool-less wound, using H. P. Reid Co (trademark). adhesive pre-coated voice-coil wire. Alternately multiple parallel smaller gauge magnet wires e.g. 46 gauge, may be used.

This high-density method of pick-up coil winding accentuates the z-axis permeability modulation of the pot-core half, increasing ramping signal build-up re: Logue U.S. Pat. No. 5,909,118 (see Oscillatory Signal Build-up above). As taught in Logue application Ser. No. 09/467,599 a polar coordinates sensor may be reduced to a ferrite pot-core half (integral x-y-z axes of permeability) having a pick-up coil of many turns wound around the central pole 284 (FIG. 1), combined with a rotating driving field generated by sine-cosine currents flowing in sine-cosine excitation windings wound through mounting hole 193 (now winding hole 193) in FIG. 1. The pot-core half must be segment-less (no lead slots)

DETAILED DESCRIPTION

Figure 1:
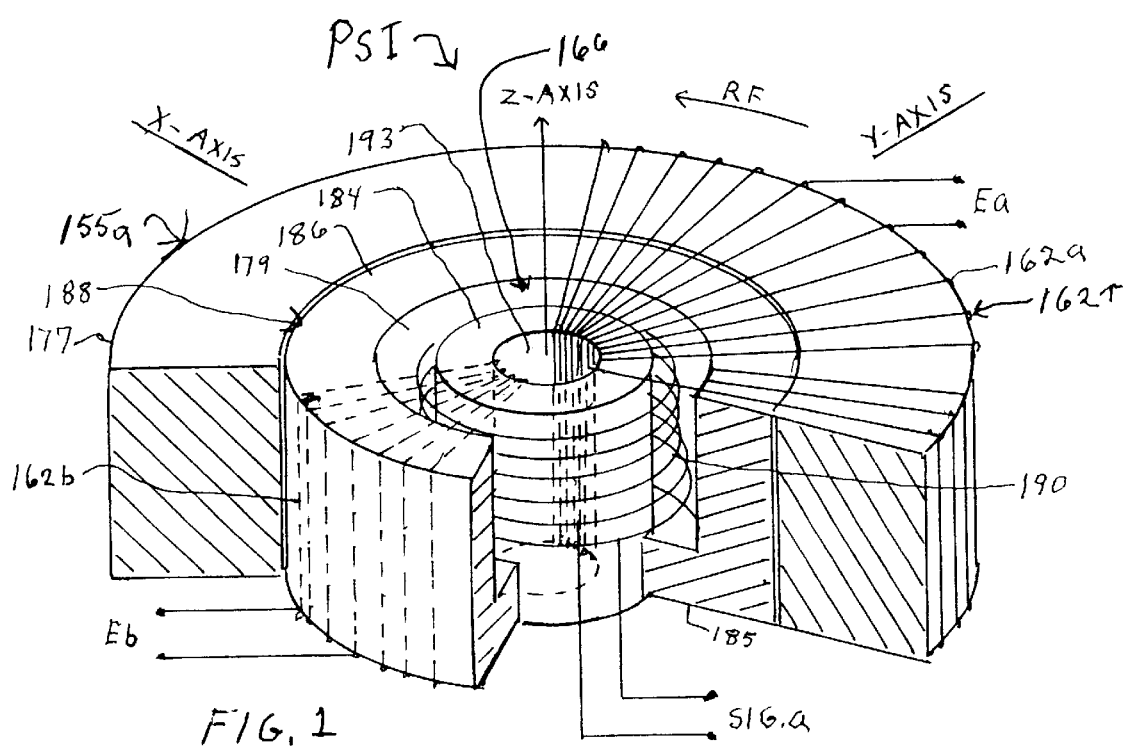
FIG. 1 is a sectional-perspective view of eddy current probe PS1 spatially illustrating the disclosed methods of increasing resolution.

Referring now to FIG. 1, illustrates an improved method of fitting a Lenz lens/caseing 177 (a higher cross-section ratio than formerly utilized) around integral driving/sensing core 188, for tighter focusing of the driving field. Previously, (cited Logue application Ser. No. 09/467,599), the prior copper Lenz lens disposition left a concentric air gap between driving-sensing core 188 and subject high cross-section Lenz lens 177.

To prevent any cutting of magnet wire insulation, Lenz lens 177 is covered with a hard insulating coating.

Another object of the disclosure is to teach a method of assembling a simple/robust eddy current probe comprising: a pot-core 188 of high permeability, a Lenz reflecting lens 177 and encompassing the x-y axes excitation winding distributions 162*t*. This novel winding method as illustrated in FIG. 1, x-y axes excitation windings 162*a*, (show in partial i.e. one quadrant represents all four quadrants) are wound through winding hole 193, encompassing integral driving-sensing pot-core 188, Lenz lens 177, and pick-up coil 190. Winding connections to all four quadrants are symbolized by leads Ea. 162*a* are. An alternate method of excitatation winding 162*b* (drawn in partial by dashed lines), which is toroidal wound through mounting hole 193 having leads Eb. For signal nulling pick-up coil 190 (having leads SIG. a) is precision wound around cylindrical pole 184 filling annular space 179. Pot-core half 188 has a base portion 185 and an open annular sensing face 166.

An object of the disclosure is to teach a simple method of signal nulling i.e. under dynamic conditions, the all encompassing excitation winding turns 162t, are individually adjusted (angularly shifted slightly) for a near flat-line null on an oscilliscope, and then glued in place. Further the described probe assembly may be encased in a cylindrical metal/plastic housing (not shown) and set in a potting compound (a thin layer covering the annular sensing face 166.)

Figure 2:
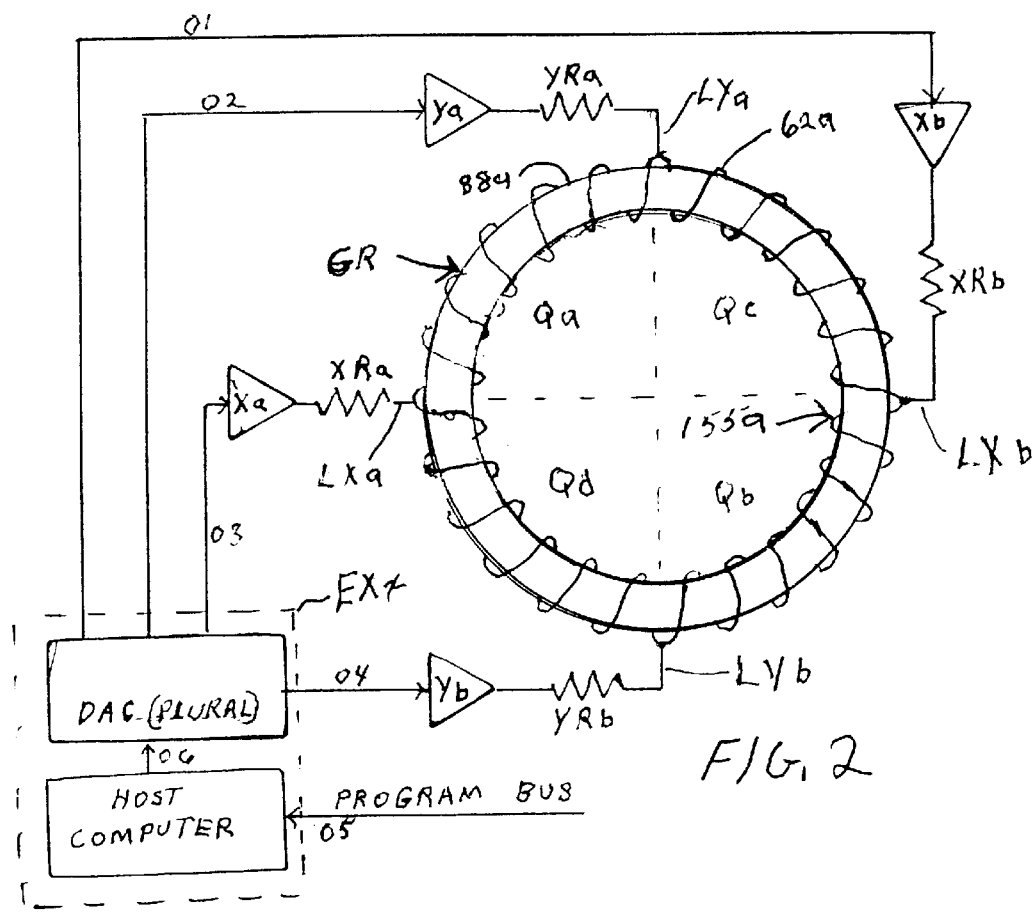
FIG. 2, is a block-circular diagram of a excitation/connection method for probe PS1 in FIG. 1.

An object of the invention is a method of sine-cosine excitation connection (including series resistors in each lead to a bipolar excitation source (FIG. 2)

Preferred Core Materials

1) Integral driving/sensing toroids: Square Permally 80, Supermalloy (tape wound), from MAGNETICS* Butler, Pa.

2) Pot-core half: Ferrite part no. 5578000721, from Fair-Rite Products Corp. Wallkill, N.Y.

Method of Driving Excitation Connections FIG. 2, digrammatically illustrates a method of: 1) sine-cosine excitation windings 162a, FIG. 1, (connections in the probe case and to the excitation source EXx.) FIG. 1, illustrates a mesh-connection (a single winding 62a in FIG. 2, is continously wound the circumference of toroid 88a) being tapped at each quadrant (x-axis taps are LXa, LXb, and y-axis taps are LYa, LYb.) This method allows the currents flowing through windings 162a, FIG. 1, to circularly equalize as in a gramme-ring GR (FIG. 2). Referring again to FIG. 2, Current to the quadrant taps LXa, LXb, LYa, LYb, are respectively fed through series resistors XRa, XRb, YRa, YRb, for enhanced differential x-y axes tilt-ability e.g. probe tilt toward quadrant Qa results in an increase of eddy current reflection in in quadrant Qa.

The gramme-ring GR, shown as a series circuit allows a differential (diametric) current-shift toward quadrant Qb. Quadrants Qc, Qd, respond to tilt in their directions in a likewise redistribution od excitation currents.

Excitation Generation

Referring again to FIG. 2. Digital values of the predetermined poly-phase sinusoidal wave shapes are loaded into the HOST COMPUTER on bus 05. The computer generated digital values are fed to plural digital-to-analog converters DAC (PLURAL) by bus 06. The analog waveforms are carried by buses 01–04 to the x-y axes amplifiers Xa, Xb, Ya, Yb, and from there to the respective series resistors XRa, XRb, YRa, YRb.

Other Excitation Methods

Just as a toroidal deflection yoke around the neck of a TV picture tube magnetically moves the electron beam/s to any location on the screen according to a predetermined program, so also the subject method moves the eddy current on (horizonal-vertical) x-y coordinates (FIG. 1).

As part of this disclosure, an eddy current scan pattern similar to a television raster may be generated in a planar workpiece by the polar coordinates probe utilizing a programable (software) method. Radar display type scans e.g. plan-position indicator (PPI) is also covered as a programable method of eddy current excitation for extending resolution (both cylindrical and planar workpieces). It is contemplated these excitation methods would be useful for detecting aircraft flaws.

Concentric Pot-core Halves

Figure 3:
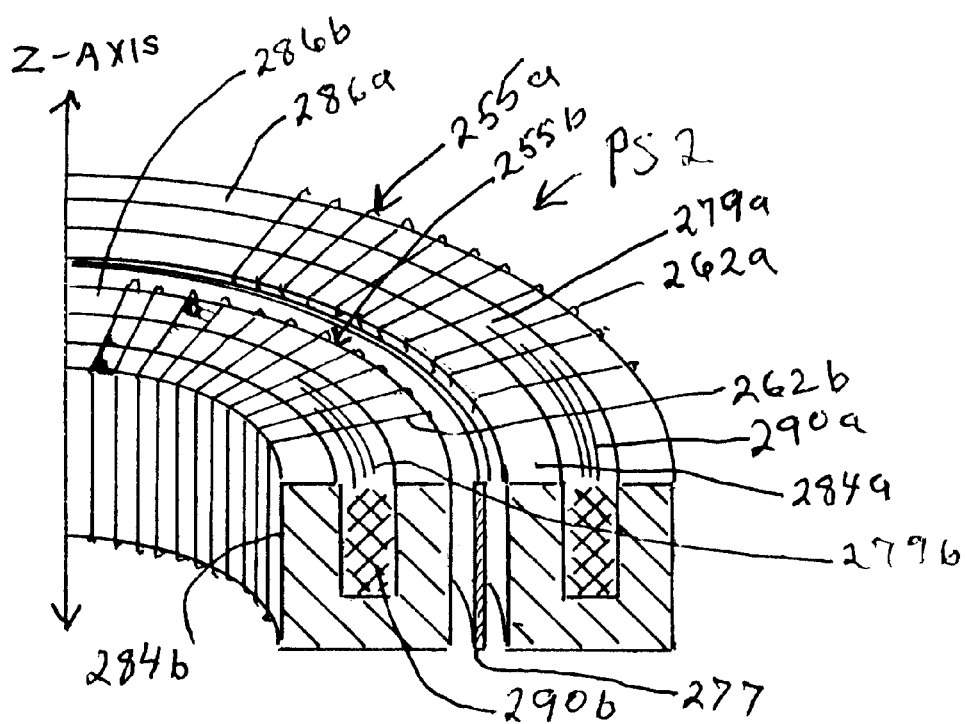
FIG. 3, is a perspective-quadrant view of an eddy current probe utilizing concentric integral driving-sensing pot-core halves on increasing radii.

In light of cited Logue U.S. Pat. No. 6,265,871B1 combined with the present teachings on integral driving-sensing pot-core halves wound according to this discription, obviously pot-core halves of increasing radii may be disposed concentrically as shown in FIG. 3 (a perspective-quadrant view of probe PS2). The concentric probe in Logue U.S. Pat. No. 6,265,871B1 utilized a plurality of toroid cores, whereas the present concentric probe PS2 employs a plurality of concentric pot-core halves 255a, 255b.

Eddy current probe PS2, includes in the outer radius, a wound integral driving-sensing toroidal core 255a, (a pot-core of enlarged diameter.) Core 255a is fully circumferentially wound with poly-phase excitation windings 262a, (leads not drawn) and is formed of a high permeability material with an annular pick-up coil groove 279a.

Core 255a has outer and central poles 286a, 284a.

Pick-up coil 290a in concentrically disposed in groove 279a (leads not shown) generating a first flaw signal. Integral driving-sensing pot-core 255b, is formed of a high permeability material, having outer and central poles 286b, 284b, leaving an annular pick-up coil space 279b. A pick-up coil 290b is wound within groove 279b for generating a second flaw signal. Poly-phase windings 262b are wound around core 255b. Ascending. reference number 277 (the lesser reference number 177 in FIG. 1, being the precedent) represents a concentrically interposed Lenz lens between cores 255a, 255b.

We claim:

1. A method of extending utility;

in a toroidal plane sensing face eddy current probe for detecting a flaw in a conducting workpiece by means of detecting an asymmetry in a rotating hemispherical driving field, said probe comprising:
a torus core formed of a high permeability material having a poloidal coil space, and;
said torus core further formed with an annular groove extending axially from the poloidal coil space to the core surface, said core taking the shape of a pot-core half, and;
poly-phase excitation winding distributions wound through the toroid window to symmetrically cover the core surface;
ramping poly-phase excitation currents being applied to the said excitation winding distributions for inducing a rotating driving dipole, fringing from the toroidal plane, for inducing a hemispherical eddy current pattern in said workpiece;
a poloidal coil being wound concentrically within the said poloidal coil space, and having connecting leads;
the said method of extending probe utility comprising:
utilization of the said poloidal coil as a pick-up coil as the said means for detecting an asymmetry in the rotating hemispherical driving field;
said pick-up coil shunted by a variable capacitor to form an oscillatory tank circuit for building up a flaw signal.

2. Method of increasing eddy current resolution;

in a toroidal plane sensing face eddy current probe for detecting a flaw in a conducting workpiece by means of detecting an asymmetry in a rotating hemispherical driving field, said probe comprising:
a toroidal core formed of a high permeability material taking the shape of a pot-core half, and;

said pot-core half further comprising:
  a central cylindrical-pole, concentrically surrounded by a cylindrical outer pole, leaving an interposed annular pick-up space, and a base portion for connecting these two poles at one end, a cylindrical winding hole concentrically disposed in the central cylindrical pole, and extending the axial length of the pot-core half, the opposite end forming an annular sensing face, and;
a pick-up coil of many turns wound around the central pole for the detecting the said asymmetry in the driving field and generating a flaw signal;
  said pick-up coil shunted by a variable capacitor to form an oscillatory tank circuit for building up a flaw signal;
  poly-phase excitation winding distributions, having connecting leads wound through the said winding hole, and around the outer pole to symmetrically cover the pot-core half circumference, forming an integral driving-sensing assembly;
  a high reluctance non-ferrous cylindrical case concentrically surrounding the integral driving-sensing assembly, and
  ramping poly-phase excitation currents being applied to the said excitation winding distributions for inducing a rotating driving dipole, fringing from the toroidal plane, for inducing a hemispherical eddy current pattern in said workpiece;
  the said method of increasing eddy current resolution comprising the steps of:
    i) tightly fitting the high reluctance non-ferrous cylindrical case coaxially around the said pot-core half, before winding the said excitation winding distributions as to encircle the said case, the pot-core radius, and the pick-up coil radius, for tighter focusing of said driving field, providing the said increased resolution;
    iii) said excitation winding distributions being mesh-connected as a gramme-ring configuration for a more circular driving field and less tilt error.

3. The method according to claim 2, wherein the said mesh-connected gramme-ring is configured for a 3 phase excitation source.

4. The method according to claim 2, wherein the said mesh-connected gramme-ring is configured as a four pole 2-phase motor stator for one rotation of the said driving field during two complete cycles of a sine-cosine excitation source.

* * * * *